(12) United States Patent
Inouye et al.

(10) Patent No.: US 12,702,553 B2
(45) Date of Patent: Aug. 11, 2026

(54) IMPLANT DEVICES, SYSTEMS, AND METHODS FOR ANNULUS REDUCTION

(71) Applicant: Boston Scientific Scimed, Inc., Maple Grove, MN (US)

(72) Inventors: Joshua Mark Inouye, Brooklyn Park, MN (US); Levi Wolterstorff, Saint Paul, MN (US); Padraig J. Savage, Santa Rosa, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1216 days.

(21) Appl. No.: 17/553,269

(22) Filed: Dec. 16, 2021

(65) Prior Publication Data

US 2022/0192828 A1 Jun. 23, 2022

Related U.S. Application Data

(60) Provisional application No. 63/126,755, filed on Dec. 17, 2020.

(51) Int. Cl.
*A61F 2/24* (2006.01)

(52) U.S. Cl.
CPC .......... *A61F 2/2445* (2013.01); *A61F 2/2442* (2013.01); *A61F 2/2466* (2013.01)

(58) Field of Classification Search
CPC ...... A61F 2/2442; A61F 2/2445; A61F 2/246; A61F 2/2466
See application file for complete search history.

(56) References Cited

U.S. PATENT DOCUMENTS

| | | | |
|---|---|---|---|
| 9,180,005 | B1 | 11/2015 | Lashinski et al. |
| 9,192,471 | B2 | 11/2015 | Bolling |
| 9,610,156 | B2 | 4/2017 | Lashinski |
| 9,622,862 | B2 | 4/2017 | Lashinski et al. |
| 9,795,480 | B2 | 10/2017 | Bolling et al. |
| 9,848,983 | B2 | 12/2017 | Lashinski et al. |
| 10,321,999 | B2 | 6/2019 | Glenn et al. |
| 10,335,275 | B2 | 7/2019 | Lashinski et al. |

(Continued)

FOREIGN PATENT DOCUMENTS

WO 2020247441 A1 12/2020

OTHER PUBLICATIONS

International Search Report and Written Opinion dated Apr. 7, 2022 for International Application No. PCT/US2021/063811.

*Primary Examiner* — William H Matthews
(74) *Attorney, Agent, or Firm* — Seager, Tufte & Wickhem, LLP

(57) ABSTRACT

An implantable device which shifts between a collapsed configuration and an expanded configuration. The implantable device may be delivered transluminally in a collapsed delivery configuration to a treatment site, whereupon the implantable device may be expanded to a deployment configuration. As the implantable device is expanded to the deployment configuration, the proximal end of the implantable device remains coupled to a delivery and/or deployment device. The implantable device is configured such that while the proximal end may be constrained by being coupled to the delivery device, the distal end is not impeded from expanding to within greater than 90% of its fully expanded configuration when not coupled to the delivery device.

18 Claims, 5 Drawing Sheets

(56) References Cited

U.S. PATENT DOCUMENTS

| | | | |
|---|---|---|---|
| 10,548,731 B2 | 2/2020 | Lashinski et al. | |
| 10,555,813 B2 | 2/2020 | Lashinski et al. | |
| 2009/0062901 A1* | 3/2009 | McGuckin, Jr. ...... | A61F 2/2418<br>623/1.3 |
| 2010/0249920 A1 | 9/2010 | Bolling et al. | |
| 2017/0135816 A1 | 5/2017 | Lashinski et al. | |
| 2018/0228610 A1 | 8/2018 | Lashinski et al. | |
| 2019/0029827 A1 | 1/2019 | Bar et al. | |
| 2019/0083243 A1 | 3/2019 | Hariton et al. | |

* cited by examiner 200
220
222
214
211
212
232
230
213
220
222
214
211
200
212
210
232
230
213

IMPLANT DEVICES, SYSTEMS, AND METHODS FOR ANNULUS REDUCTION

PRIORITY

The present application is a non-provisional of, and claims the benefit of priority under 35 U.S.C. § 119 to, U.S. Provisional Application Ser. No. 63/126,755, filed Dec. 17, 2020, the disclosure of which is hereby incorporated herein by reference in its entirety for all purposes.

FIELD

The present disclosure relates generally to the field of implantable medical devices. More particularly, the present disclosure relates to medical devices, systems, and methods for cardiac treatment, such as annuloplasty.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques, including transcatheter repair, have been introduced that aim to restore a mitral valve to its native or an improved configuration, for example by implanting an annuloplasty ring or other implantable annuloplasty device around the valve annulus to cinch the valve to the desired improved configuration. It is generally desirable to deliver an annuloplasty device in a minimally invasive manner (e.g., percutaneously and transluminally/endoluminally, such as transfemorally, transeptally, or transapically). Such delivery generally requires the annuloplasty device to shift between a compact delivery configuration and an expanded deployment configuration. The delivery system generally does not expand with (or at least to the same extent as) the annuloplasty device. Accordingly, a proximal end of the annuloplasty device which remains coupled to the delivery system during deployment of the annuloplasty device may inhibit expansion of the distal end of the annuloplasty device secured to the valve annulus. More particularly, the proximal end of the annuloplasty device remains attached to the delivery device as the distal end of the annuloplasty device is expanded. Because the delivery device does not expand with the annuloplasty device, the proximal end of the annuloplasty device may hold back the distal end from expanding completely (e.g., causing the distal end to "kick in" or pivot inwardly). Solutions for or reductions of such potential diameter loss at the distal end of an annuloplasty device would increase the patient population that can be treated with the annuloplasty device.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an implantable device, shiftable between a collapsed configuration and an expanded configuration, includes a tubular frame extending about a frame axis and having a proximal end configured to be coupled to a delivery device and a distal end configured to be secured to tissue. The tubular frame has a proximal section adjacent the proximal end of the frame, an anchoring section adjacent the distal end of the frame, and a middle section between the proximal section and the anchoring section. The proximal section extends at an angle relative to the middle section in a direction outwardly from the frame axis at least when the implantable device is expanded prior to being implanted. The distal section extends at an angle relative to the middle section in a direction inwardly towards the frame axis.

In some embodiments, the tubular frame comprises a plurality of struts joined along proximal apices.

In some embodiments, a bend is provided adjacent and spaced from the proximal end of the tubular frame to define the proximal section relative to the middle section. In some embodiments, the tubular frame comprises a plurality of struts joined along proximal apices, and the bend is formed adjacent at least one of the proximal apices.

In some embodiments, a slider is provided, and is movable to shift the implantable device between a collapsed configuration and an expanded configuration. In some embodiments, the tubular frame comprises a plurality of struts joined along proximal apices, and the slider is provided on the at least one proximal apex, and is movable along the at least one proximal apex to shift the implantable device between a collapsed configuration and an expanded configuration.

In some embodiments, distal movement of a slider causes the proximal section of the frame to straighten relative to the middle section of the frame. In some embodiments, distal movement of the slider over a bend in the frame separating the proximal section from the middle section causes the proximal section of the frame to straighten relative to the middle section of the frame. In some embodiments, a slider screw is held in a window in the at least one proximal apex by one or more bearings; the slider is movable along the at least one apex upon rotation of the slider screw; and the slider screw pivots with respect to the at least one apex to pivot the slider with respect to the apex, the slider forming the proximal section of the tubular frame. In some embodiments, the slider forms the proximal section of the frame and is pivotable between a configuration at angle relative to the middle section of the frame to a configuration substantially aligned with the middle section of the frame.

In accordance with various principles of the present disclosure, a delivery system includes a delivery catheter, a delivery device deliverable through the delivery catheter to a treatment site, and an implantable device having a proximal end coupled to the delivery device and a distal end configured to be secured to tissue at the treatment site, the implantable device deliverable through the delivery catheter to the treatment site. The delivery device includes at least one elongated member. The implantable device is expandable from a collapsed delivery configuration to an expanded deployment configuration while coupled to the delivery device. A proximal section of the implantable device adjacent the proximal end of the implantable device remains at a smaller angle with respect to the at least one elongated member of the delivery device than does a middle section of the implantable device extending distally from the proximal section when the implantable device shifts from the collapsed delivery configuration to the expanded deployment configuration while coupled to the delivery device.

In some embodiments of a delivery system, the implantable device includes a tubular frame, and a bend is provided adjacent and spaced from the proximal end of the tubular frame to form the proximal section of the implantable device. In some embodiments, the tubular frame includes a plurality of struts joined along proximal apices, and the bend is formed adjacent at least one of the proximal apices. In some embodiments, the implantable device further includes a slider on the at least one of the proximal apices, the slider movable along the at least one proximal apex to shift the implantable device between a collapsed configuration and an expanded configuration. In some embodiments, the slider is slidable over the bend.

In some embodiments of a delivery system, the tubular frame of the implantable device includes a plurality of struts joined along proximal apices, a slider provided on at least one of the proximal apices and movable along the at least one proximal apex to shift the implantable device between a collapsed configuration and an expanded configuration, and a slider screw. The slider screw is held in a window in the at least one proximal apex by one or more bearings. The slider is movable along the at least one apex upon rotation of the slider screw, and the slider screw pivots with respect to the at least one apex to pivot the slider with respect to the apex, the slider forming the proximal section of the tubular frame.

In some embodiments of a delivery system, an anchoring bend is provided in the frame defining an anchoring section adjacent a distal end of the implantable device, and the anchoring section extends at a smaller angle with respect to the at least one elongated member of the delivery device than does the middle section of the implantable device.

In accordance with various aspects of the present disclosure, a method of delivering and deploying an implantable device to a cardiac valve annulus includes delivering the implantable device via a delivery catheter to the cardiac valve annulus with a proximal end of the implantable device coupled to a delivery device; expanding the distal end of the implantable device; and allowing a distal section of the implantable device to extend away from the delivery device at a greater angle than the angle at which a proximal section of the implantable device extends away from the delivery device. In some embodiments, the implantable device that is delivered and deployed includes a tubular frame comprising a plurality of struts joined along proximal apices with at least one slider on at least one of the proximal apices, the method further including moving the slider with respect to the at least one proximal apex to allow the distal section of the implantable device to extend away from the delivery device at a greater angle than the angle at which a proximal section of the implantable device extends away from the delivery device.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
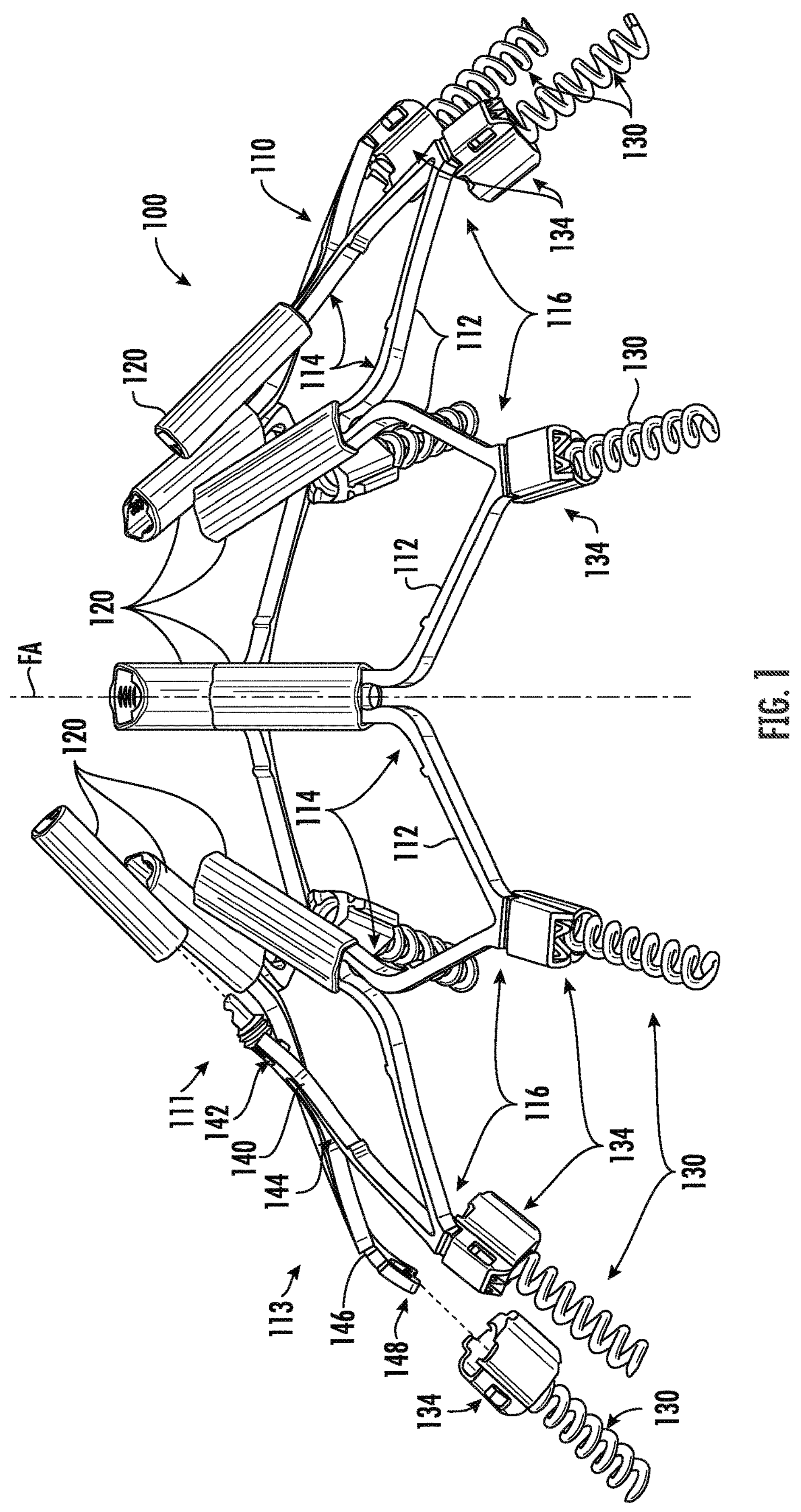
FIG. 1 is a perspective view of an example of an implant device formed in accordance with various principles of the present disclosure, with a slider shown in an exploded position spaced away from the frame of the device, and with an anchor and anchor housing shown in an exploded position spaced away from the frame of the device.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various aspects of the present disclosure, an implantable device which shifts between a collapsed configuration and an expanded configuration is shaped and configured to be unaffected (or at least minimally affected) by being coupled at its proximal end with a delivery device which does not expand or extend away from its delivery configuration to as great an extent as the distal end of the implantable device expands from its delivery configuration. More particularly, the implantable device shifts between a collapsed configuration for deployment, which may be referenced herein as a collapsed deployment configuration for the sake of convenience and without intent to limit, and an expanded configuration. It is generally desirable for the expanded configuration of the device to be as large as possible when deployed for placement with respect to the treatment site so that the implantable device may be used with the greatest range of treatment site widths/dimensions. Once the implantable device is secured in place at the treatment site, the implantable device may be collapsed as needed or indicated to reconfigure the treatment site. It will further be appreciated that terms such as secure (and conjugations thereof) with reference to the implantable device and the treatment site may be used interchangeably herein with terms (and conjugations thereof) such as affix, implant, couple, engage, anchor, hold, retain, etc., without intent to limit. It will further be appreciated that movement or reconfiguring of the implanted implantable device to reduce the size of the treatment site (e.g., a valve annulus diameter) is alternately referenced herein as cinching (including various conjugations thereof).

The implantable device is sized and dimensioned to be readily deliverable through narrow and/or tortuous pathways or lumens in the human body as part of a delivery system which includes a delivery device. For instance, the delivery system may be sized and dimensioned for transluminal or endoluminal delivery, such as percutaneous delivery (including, without limitation, transfemoral, transseptal, and transapical delivery), to a treatment site within the body. The term treatment site may alternately be referenced herein as an implant site or site of implantation or the like, without intent to limit. The implantable device in its delivery configuration has an overall widthwise dimension (the smaller dimension of the implantable device, generally in a direction transverse to the longitudinal axis of the delivery system and the direction along which the implantable device is delivered to a treatment site) sized to fit within a tubular delivery device sized and configured to fit within and navigate through tortuous pathways or lumens in the human body. The tubular delivery device may be a shaft, lumen, catheter, endoscope, tube, tubular flexible elongate member, or the like, such terms being used interchangeably herein without intent to limit, and generally is referenced as a delivery catheter for the sake of convenience and without intent to limit. The delivery device is coupled to the implantable device to assist with navigating the implantable device to the treatment site. The delivery device may include a plurality of flexible elongate members capable of actuating one or more components of the implantable device to cause the implantable device to expand or collapse and/or to anchor the implantable device to the treatment site. The flexible elongate member may include latches at distal ends thereof which engage or couple with latch couplers on various movable (e.g., rotatable) components on the implantable device. The flexible elongate members may be alternately referenced herein as actuators or drivers or controllers (with or without the term "mechanism") or the like, without intent to limit, and may be in the form of wires or tubes or cables or the like, as known or heretofore known in the art. The delivery device thus may also be considered a deployment device with components used to deploy and/or secure the implantable device in place at the treatment site. For the sake of simplicity, references herein to a delivery device should be considered to be references to a delivery device and/or a deployment device (with such devices optionally being embodied by common structures) An additional flexible elongate tubular member may extend over at least one and preferably each of the flexible elongate members to hold the latch at the end of the flexible elongate member in place with respect to (in engagement with) the latch coupler on the corresponding movable component on the implantable device.

Generally, a delivery device for an implantable device of the present disclosure is relatively stiff to be able to deliver the implantable device (e.g., by navigating tortuous pathways) to the treatment site. The delivery device generally also is relatively stiff to be able to transmit the desired actuation forces (e.g., torque) to various components of the implantable device, such as to shift the implantable device from the delivery configuration to the deployment configuration and/or to a final implanted configuration (which may be smaller than the deployment configuration) and/or to implant the implantable device at the treatment site. Accordingly, the delivery device generally cannot make sharp turns upon exiting a delivery catheter. For instance, the delivery device may extend outwardly from the delivery catheter at generally no more than 45° with respect to the delivery axis (the extent or direction along which the implantable device is delivered to the treatment site). Of course, it will be appreciated that the maximum allowable angle at which the delivery device extends from the delivery catheter may vary depending on the actual device and delivery system geometries and mechanical properties. Moreover, delivery systems which are transcatheter devices generally have a small diameter (approximately 10 mm) compared with the diameter of the implantable device when expanded (for instance, approximately 50 mm on the distal end, and approximately 25 mm on the proximal end), and, accordingly, the associated flexible elongate members must flare outward from the small diameter delivery system to attach to the larger expanded implant. Prior art implantable devices with similar structures/configurations as the implantable device disclosed herein (other than the improved structures/configurations disclosed herein) have generally been inhibited from completely expanding while the proximal end of the implantable device remains coupled to the delivery device. The proximal end of the implantable device, while coupled to the delivery device, cannot expand significantly from its delivery configuration (yet generally expands further, once released therefrom), and causes prior art implantable devices to give a bit and/or rotate and/or pivot or otherwise conform towards the delivery device as well. Accordingly, the distal end of the prior art implantable devices has been inhibited from reaching its maximum possible expansion dimension (such as may be reached when the implantable device is not coupled to the delivery device).

Despite the proximal end of the implantable device of the present disclosure being coupled to a delivery device which does not expand significantly from its delivery configuration, the distal end of an implantable device formed in accordance with principles of the present disclosure is not appreciably inhibited (by the delivery device) from expanding. More particularly, in contrast with a distal section thereof, a proximal section of an implantable device formed in accordance with various principles of the present disclosure remains more closely aligned with, or more closely corresponds with, the longitudinal axis of the delivery device and/or the delivery catheter via which the implantable device is delivered to the treatment site. In some embodiments, the implantable device is structured so that a distally-extending section of the frame may flare or extend outwardly from the delivery device at a greater angle than a proximal section of the frame coupled to the delivery device.

The implantable device may be described as having a device axis about which the device extends and which generally is aligned with the longitudinal axis of the delivery catheter (along which the implantable device is delivered) and/or the elongate extent of the delivery device. In some embodiments, the implantable device includes a tubular frame extending about a device axis which may be considered a frame axis. A proximal section of the tubular frame of an implantable device formed in accordance with principles of the present disclosure may remain more closely aligned with the frame axis than an adjacent (e.g., adjoining) more distal section of the frame when the implantable device is coupled to a delivery device and/or when the implantable device is in a neutral configuration (unattached to and not constrained by another device). The proximal section generally is the section coupled to the delivery device and may be considered the proximal-most section of the frame. The section adjacent and more distal to the proximal section, and extending away from the frame axis at a greater angle than does the proximal-most section, may be considered a middle section. The distal-most section of the frame may be secured to the treatment site such as with anchor assemblies which may be mounted on the distal-most section. In order to achieve the desired expansion, anchoring, and cinching mechanics, the distal-most section of the frame, generally is shorter than the middle section and angled inwardly towards the frame axis (relative to the middle section of the frame).

In accordance with one aspect of the present disclosure, a proximal end of an implantable device formed in accordance with principles of the present disclosure is shaped out of its typical plane (as in prior art devices) such as by being bent outwardly with respect to a distal end of the implantable device. Such bend (alternately referenced herein as a "bend-back" without intent to limit) permits expansion of the implantable device from a collapsed delivery configuration to an expanded deployment configuration without being inhibited by the proximal end of the implantable device remaining coupled to a delivery device which does not (or cannot) expand to the same extent as the distal end of the implantable device expands. As a result, the section of the implantable device distal to the bend-back section (which may be the proximal-most section of the frame) extends away from the bend-back section when the implantable device is coupled to a delivery device, thereby expanding to a further extent than possible without the bend-back section. The bend-back angles a proximal section outwardly with respect to a more distal section of the implantable device a sufficient degree to allow the proximal end of the implantable device to remain coupled to the delivery device without significantly inhibiting expansion of the distal end of the implantable device. For instance, the bend-back may allow the implantable device to expand to at least about 90% and preferably to at least about 95% and even more preferably to at least about 96% or more (including increments of 0.1% from 90% to 100%) of its fully expanded dimension, and even more preferably to the full expanded dimension when not coupled to the delivery device. In some embodiments, the diameter when attached to a delivery device could actually become larger than the free state diameter (when not coupled to a delivery device), such as if the delivery device tilts the bend-back section inwards and thus tilts the more distal section of the implantable device outwards, resulting in a greater diameter at the distal end of the implantable device. It will be appreciated that the bend-back section of the implantable device may be shorter than the remaining section of the implantable device to allow the greatest amount of expansion of the distal end of the implantable device.

The bend-back portion may be positioned sufficiently proximal to the proximal end of the implantable device to be captured with a slider or cinch sleeve used to shift the implantable device into a collapsed configuration. As such, the bend-back does not cause the distal end to flare outward when the implantable device is in the collapsed delivery configuration, and in various cinched configurations. The favorable cinch mechanics of the implantable device are thus maintained.

In accordance with another aspect of the present disclosure, which may be separate and independent of the first aspect, or combinable therewith, a component of the implantable device is movable to shift the implantable device between the various configurations thereof (e.g., to expand or contract the implantable device). For instance, a component of the implantable device may be pivotable with respect to a frame of the implantable device and/or the anchoring components of the implantable device (configured to anchor the implantable device to tissue at the treatment site). The pivotable component pivots to a sufficient degree to allow the proximal end of the implantable device to remain coupled to the delivery device without significantly inhibiting expansion of the distal end of the implantable device. For instance, the pivotable component may allow the implantable device to expand to at least about 90% and preferably to at least about 95% and even more preferably to at least about 96% or more (including increments of 0.1% from 90% to 100%) of its fully expanded dimension, and even more preferably to the full expanded dimension when not coupled to the delivery device. The pivotable component may pivot back to be substantially aligned with the frame of the implantable device when the implantable device is shifted from an expanded configuration towards a collapsed configuration. As such, the pivotable component enables favorable cinch mechanics of the implantable device.

In one embodiment, the implantable device is an annuloplasty device having a generally tubular frame with a proximal end and a distal end. The proximal end of the frame is coupled to a delivery device. A slider may be provided on the frame, such as the proximal end of the frame, to adjust the configuration (e.g., collapse or expansion) of the frame. It will be appreciated that the term slider is used for the sake of convenience and may be used interchangeably herein with such terms as collar or sleeve or cinch sleeve or slider sleeve or nut without intent to limit. The distal end of the frame carries two or more anchors that are implanted into tissue (e.g., a cardiac valve annulus) at the treatment site to secure the frame at the treatment site. In some embodiments, the frame is formed of a plurality of struts, adjacent struts forming a proximal apex at a proximal end of the frame and a distal apex at the distal end of the frame. In an embodiment in which the frame has at least one proximal apex, a slider may be provided over at least one proximal apex and may be moved distally or proximally to adjust the distance between the struts forming the apex to adjust the configuration (e.g., collapse or expansion) of the frame. In an embodiment in which the frame has at least one distal apex, at least one anchor may be provided on at least one distal apex to anchor the implantable device with respect to tissue. The slider and/or anchor may be adjusted or actuated by the delivery device, such as by a rotational movement. However, other configurations are within the scope and spirit of the present disclosure.

Various embodiments of an implantable device and associated systems and methods of implantation with respect to a treatment site will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, it will be appreciated that in the following description, elements or components similar among the various illustrated embodiments are generally designated with the same reference numbers increased by a multiple of 100 and redundant description is omitted. Common features are identified by common reference elements and, for the sake of brevity, the descriptions of the common features are generally not repeated. For purposes of clarity, not all components having the same reference number are numbered.

An example of an implantable device 100 which may be formed in accordance with principles of the present disclosure is an implantable annuloplasty device, for custom reshaping of a heart valve (e.g., the mitral valve, or the tricuspid valve), such as illustrated in FIG. 1. The illustrated example of an implantable device 100 includes a frame 110 that may form a generally tubular shape extending about a frame axis FA. As used herein, the term "tubular" is to be understood to include circular as well as other rounded or otherwise closed shapes. As referenced herein, the frame axis FA is the axis relative to which the distal end 113 of the frame 110 extends outward when the frame 110 is expanded. In an embodiment of a frame 110 which is generally circular, the frame axis FA is a central longitudinal axis of the frame 110.

Figure 2:
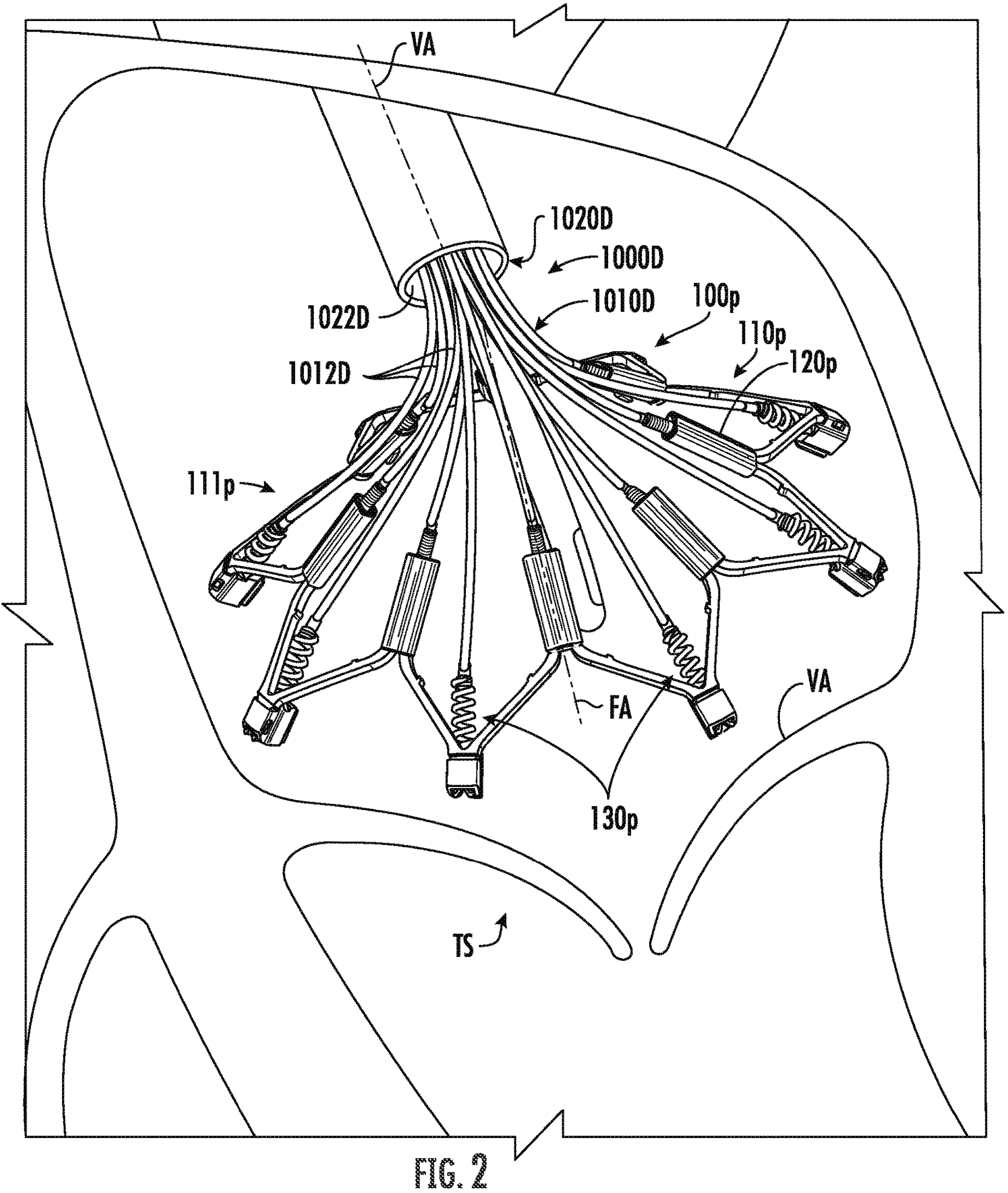
FIG. 2 is a perspective view of an example of a delivery device delivering a prior art implant device to a treatment site illustrated schematically.

The frame 110 may assume various shapes, sizes, dimensions, configurations, etc. during different phases of deployment such as during pre-delivery, delivery, tissue engagement, anchoring, adjustment (e.g., cinching), etc. For example, the frame 110 may be configured to change shape, size, dimension, and/or configuration, such as to modify the shape, size, dimension, configuration, etc. of the valve annulus (or other structure) to which it is coupled. The implantable device delivery system (of which the implantable device 100 may be a part) preferably is configured to be delivered in a minimally invasive manner, such as for transluminal delivery to the heart. Accordingly, the implantable device 100 is delivered in a compact delivery configuration (similar to the configuration illustrated in FIG. 4, but with the overall diameter reduced as much as possible to fit the implantable device 100 within a delivery catheter 1020 such as illustrated in FIG. 2). It will be appreciated that the term compact may be used interchangeably herein with such terms as collapsed or compressed or simply unexpanded without intent to limit. The implantable device 100 is expandable into a expanded configuration for deployment, placement with respect to the treatment site TS, anchoring to the treatment site TS, etc. The implantable device 100 may expand naturally (e.g., may be self-expandable), for example if the frame is formed of a shape memory or superelastic material (e.g., Nitinol) that is biased towards an expanded state. Alternatively, or additionally, the implantable device

100 may expand with assistance of an expansion device or mechanism, for example through the use of a force applied within the frame such as using an expandable deployment device (e.g., an inflatable balloon or the like). In a relaxed configuration, the frame 110 splays outwardly from the proximal end 111 to the distal end 113 thereof. Generally, expansion or contraction of the overall size (widthwise) of the frame 110 is controlled adjacent the proximal end 111 of the frame 110.

In the illustrated embodiment, one or more sliders 120 are provided to adjust the configuration of the frame 110, as will be described in further detail below. Typically, the implantable device 100 is delivered in a compact delivery configuration, expanded from the delivery configuration into an expanded deployment configuration for positioning relative to the treatment site and deployment (e.g., anchoring in place), implanted (e.g., with the use of one or more anchors 130) in or around the treatment site (e.g., in the illustrated embodiment, secured to a valve annulus), and then contracted (alternately referenced herein as collapsed without intent to limit) as needed or indicated to reconfigure the treatment site as desired or indicated. Each slider 120 preferably is adjustable independently of the other slider 120. Such adjustment results in adjustment of at least one of the size, shape, configuration, dimension, etc., of the frame 110 to affect at least one of the size, shape, configuration, dimension, etc., of the treatment site TS (such as to restore or correct the shape of a valve annulus for proper functioning or competency thereof).

An example of a delivery system 1000D is illustrated in FIG. 2 as including an implantable device (which may be the illustrated prior art implantable device 100*p* or an implantable device formed in accordance with principles of the present disclosure, such as the implantable device 100 illustrated in FIG. 1), a delivery device 1010D, and a delivery catheter 1020D. The implantable device 100 and the delivery device 1010D are dimensioned and configured to fit within a lumen 1022D of the delivery catheter 1020D. The delivery catheter 1020D, in turn, may be dimensioned and configured to fit within a working channel of a further tubular flexible elongate member such as an endoscope (such as known in the art or heretofore known). The frame 110*p* of the implantable device 100*p* may be expanded into an operable unexpanded configuration, as illustrated in FIG. 2, once delivered to the treatment site TS, which in this embodiment is a heart valve annulus VA. Expansion of the frame 110*p* may be effected by moving the sliders 120*p* proximally, as will be described in further detail below with reference to an embodiment formed in accordance with principles of the present disclosure. Once delivered, the implantable device 100*p* is deployed and secured to the heart at the implantation site, such as with a tissue anchor 130*p*. The shape, size, dimension, configuration, etc. of the implantable device 100*p* may then be adjusted (e.g., by sliding one or more the sliders 120*p* proximally or distally with respect to the frame 110*p*) to configure the shape and/or structure of the heart valve annulus VA to which the implantable device 100 is secured, as medically indicated.

As may be appreciated with reference to FIG. 2, the delivery device 1010D includes a plurality of actuators 1012D each coupled to a slider 120*p* (to actuate the slider 120*p* to adjust the configuration of the frame 110) and/or to an anchor 130*p* (to actuate the anchor 130*p* to anchor the implantable device 100*p* in place with respect to the valve annulus VA). The actuators 1012D extend from the delivery catheter lumen 1022D and are relatively stiff so that they generally do not flex outwardly more than about 45° from the longitudinal axis LA of the delivery catheter 1020D (along which devices are delivered through the delivery catheter 1020D). Accordingly, as may be appreciated with reference to FIG. 2, the proximal end 111*p* of the frame 110*p* which is coupled to the delivery device 1010D may be somewhat restricted from pivoting as the distal end 113*p* of the frame 110*p* expands outwardly to be positioned about the valve annulus VA. Such restriction with respect to the proximal end 111*p* of the frame 110*p* generally also has a restricting effect on the distal end 113*p* of the frame 110*p*. As such, the prior art frame 110*p* may not be able to expand to its fully expanded configuration (e.g., when not coupled to the delivery device 1010D). The prior art frame 110*p* thus may not be readily usable with a relatively large valve annulus if the distal end 113*p* of the frame 110*p* cannot be sufficiently expanded to be implanted about such large valve annulus.

In accordance with one aspect of the present disclosure, and as may be appreciated with reference to FIG. 1 and FIG. 2, the frame 110 of an implantable device 100 has one or more bends 140 adjacent (yet distally spaced from) the proximal end 111 of the frame 110. The bend 140 is positioned and configured to form a bend-back section 142 in the frame 110 (a section of the frame 110 extending between the bend 140 and the proximal end 111 of the frame 110) relative to a more distal section 144 of the frame 110. The bend 140 is positioned between the bend-back section 142 and the remaining section 144 of the frame 110 and may be closer to the proximal end 111 of the frame 110 than to the distal end 113 of the frame 110 such that the bend-back section 142 is a proximal section shorter than the remaining section 144 of the frame 110. The bend-back section 142 is angled outwardly from the remaining section 144 of the frame 110 (i.e., in a direction away from the frame axis FA) when the implantable device 100 is coupled to a delivery device 1010 and/or in a neutral configuration (unattached to and/or not constrained by another device). The distal-most section of the frame 110 may be configured for anchoring the implantable device 100 to the treatment site TS, and may be considered a distal anchoring section 146 distal to the remaining section 144 of the frame 110 (which, as such, may be considered a middle section of the frame between the proximal-most bend-back section 142 and the distal-most anchoring section 146). In some embodiments, an anchoring bend 148 is provided between the remaining section 144 of the frame 110 and the anchoring section 146 to cause the anchoring section 146 to bend inwardly towards the frame axis FA so that anchors mounted on the anchoring section 146 may enter tissue at a favorable angle (e.g., approximately 55° from horizontal when coupled to a delivery device). The angle of the bend 140 defining the bend-back section 142 may be at least approximately 5° and at most approximately 45° relative to the axis along which the remaining section 144 of the frame 110 lies, in other words at least approximately 45° and at most approximately 175° relative to the remaining section 144 of the frame 110, with the bend-back section 142 extending in a direction outwardly from the frame axis FA. The angle of the anchoring bend 148 may be as little as 0° and at most approximately 45° relative to the axis along which the remaining section 144 of the frame 110 lies, in other words at least approximately 180° and at most approximately 225° relative to the remaining section 144 of the frame 110, and in a direction inwardly towards the frame axis FA (opposite the direction in which the bendback section 142 is bent). In some embodiments, the bendback section 142 is at least approximately 30% of the total length of the frame 110 and at most about 50% of the total length of the frame 110, the remaining section 144 of the frame 110 is at least about 30% of the total length of the frame 110 and at most about 50% of the total length of the frame 110, and the anchoring section 146 is at least about 10% of the total length of the frame 110 and at most about 20% of the total length of the frame 110. The length of the bend-back section 142 may be as little as approximately 25% and at most about 75% of the length of the remaining section 144 of the frame 110. In some embodiments, the length of the bend-back section 142 is approximately 2-6 mm and the length of the remaining section 144 of the frame 110 is approximately 4-8 mm.

In accordance with various principles of the present disclosure, a frame 110 formed with at least a bend-back section 142 allows the frame 110 to expand while still coupled with a delivery device 1010D (such as illustrated in FIG. 2), with the bend-back section 142 remaining more closely aligned with the delivery device 1010D than in frames of previous otherwise similar implantable devices, and the remaining section 144 of the frame 110 angling away from the delivery device 1010D to allow full expansion of the distal end 113 of the frame 110. In other words, as the frame 110 expands, the bend-back section 142 remains more upright (as in the illustrated position, or, in situ, corresponding to and more aligned with the longitudinal axis LA of the delivery catheter 1020D) and more closely aligned with the frame axis FA than does the remaining section 144 of the frame 110. The expansion of the frame 110 thus does not "fight" the connection with the delivery device 1010D as much, and the distal end 113 is able to expand to a greater extent than in prior art implantable devices without such a bend (and therefore which are more constrained by the limitations of the stiffness and/or angles of the delivery device 1010D). More particularly, the distal end 113 of the implantable device 100 is able to expand to (or close to, such as within at least about 90% and preferably at least about 95% and even more preferably at least about 96% or more, including increments of 0.1% from 90% to 100%) its fully expanded dimension when not coupled to the delivery device. For instance, in a prior art implantable device 100*p* as illustrated in FIG. 2, a fully expanded distal end 113*p* diameter when the implantable device 100*p* is not attached to a delivery device 1010D may be approximately 52 mm, whereas the landing diameter when coupled with a delivery device 1010 (the fully expanded diameter at which the implantable device 100*p* may be secured to the treatment site TS) may only be about 48 mm. In contrast, the distal end 113 of an implantable device 100 with a frame 110 similar to the prior art frame 110*p* but with a bend 140 in accordance with principles of the present disclosure may have a fully expanded diameter of approximately 54 mm when not attached to the delivery device 1010, and a landing diameter of about 52 mm when coupled to the delivery device 1010.

In the configuration illustrated in FIG. 1, the sliders 120 are positioned proximal to the bend 140 (with one slider 120 shown exploded away so that the bend 140 may be more clearly seen), and not over the bend 140. As such, the remaining section 144 of the frame 110 benefits to the full extent of the bend 140. The sliders 120 are generally positioned more distally with respect to the frame 110 when the frame 110 is in the delivery configuration (not shown), and may be moved distally relative the positions illustrated in FIG. 1 to move the frame 110 to a less expanded configuration. When the sliders 120 are distally advanced over the bend 140, the sliders 120 may straighten the bend 140 to allow the frame 110 to achieve a compact configuration substantially the same as the compact configuration as a prior art implantable devices 100*p* as illustrated in FIG. 2. Moreover, once the implantable device 100 has been anchored to tissue (e.g., a valve annulus VA) at the treatment site TS, the sliders 120 may be distally advanced to cinch the implantable device 100 to a smaller overall configuration than the expanded deployment configuration. When the sliders 120 are advanced over associated bends 140 in the frame 110, the sliders 120 may straighten the bends 140 so that the frame 110 may be in a substantially straight configuration as illustrated in FIG. 4, substantially the same as if the frame 110 had no bend 140.

Figure 3:
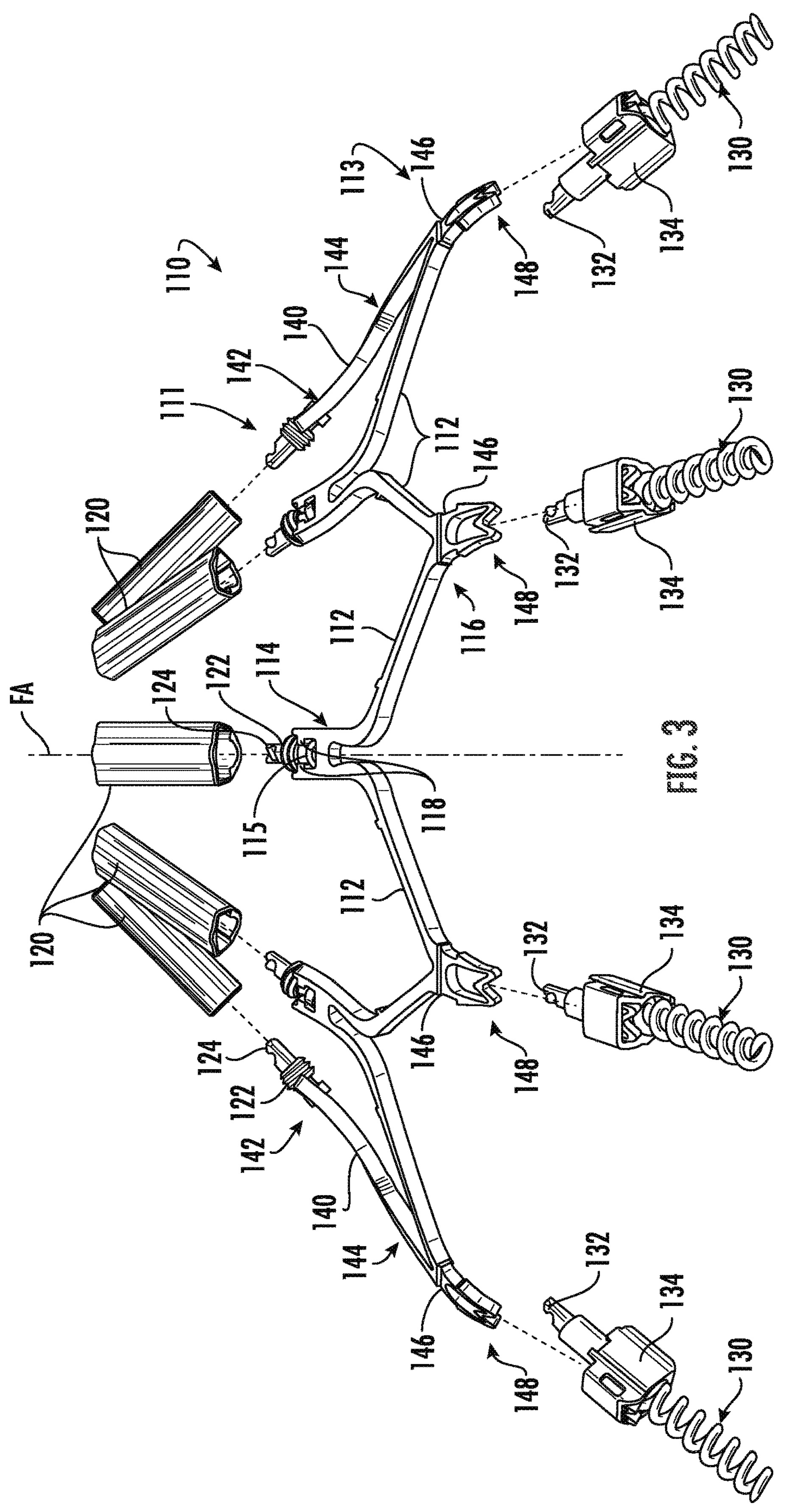
FIG. 3 is an elevational view of an implant device formed in accordance with various principles of the present disclosure, such as in FIG. 1, in a deployed uncinched configuration, with the sliders and anchor assemblies shown in an exploded position spaced away from the frame of the device.

In the embodiment illustrated in FIG. 1 and FIG. 3, the slider 120 may be advanced distally or retracted proximally with respect to the frame 110 upon rotation of a slider actuator screw 122 (referenced herein as a screw for the sake of simplicity and without intent to limit). The screw 122 has external threads engaging corresponding internal threads within the slider 120. Because the screw 122 is held axially with respect to the frame 110, rotation of the screw 122 causes axial advancement of the slider 120 with respect to the screw 122. The screw 122 may be provided with a latch coupler 124 for engaging a latch of an actuator 1012D which rotates the screw 122.

Figure 4:
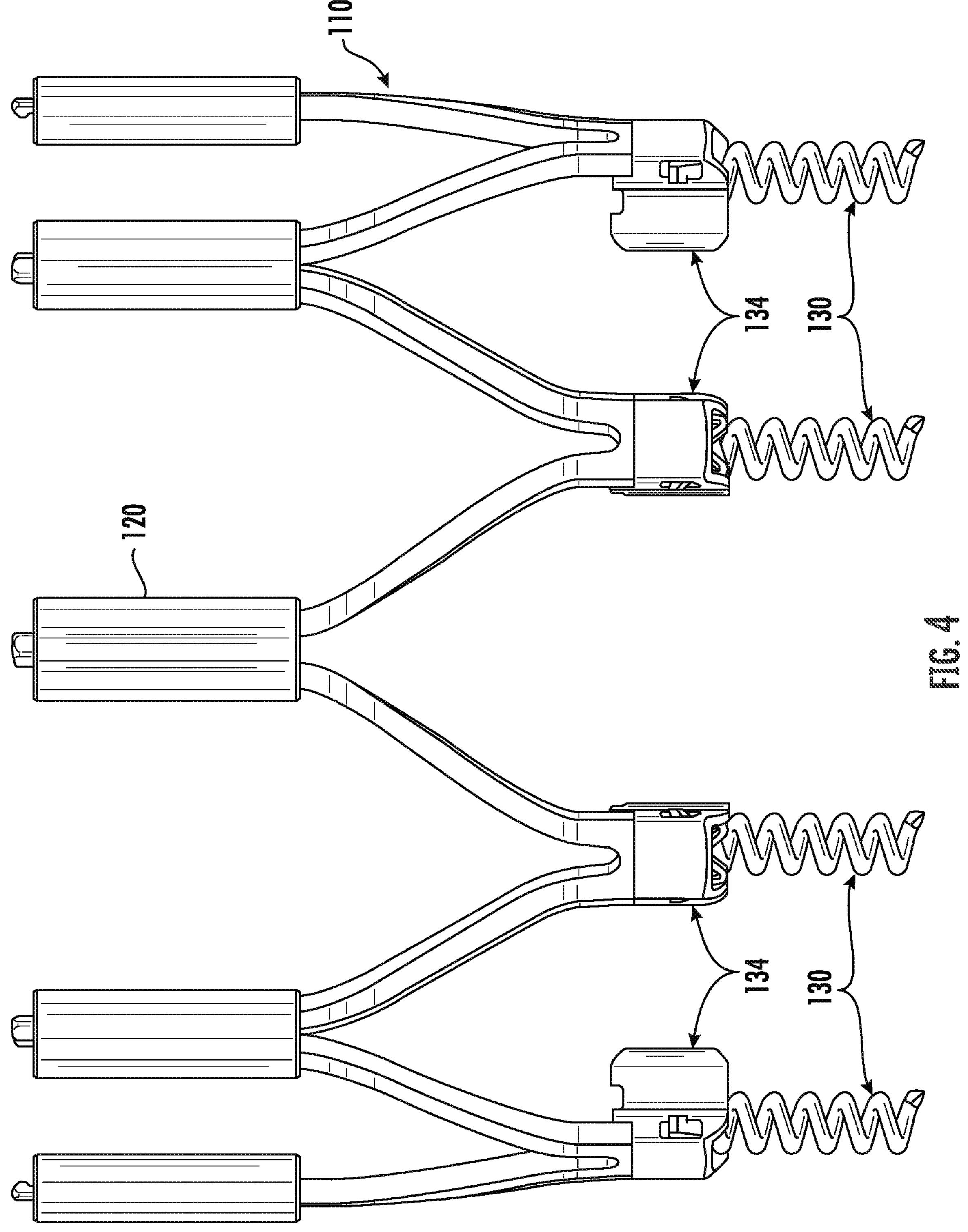
FIG. 4 is an elevational view of an implant device formed in accordance with various principles of the present disclosure, such as in FIG. 1, in a cinched configuration.

In some embodiments, such as illustrated in FIGS. 1, 3, and 4, the frame 110 is formed from one or more struts 112 that may form all or part of the frame 110. The struts 112 may include elongated structural members formed of a metal alloy, a shape memory material, such as an alloy of nickel titanium or other metals, metal alloys, plastics, polymers, composites, other suitable materials, or combinations thereof. In one embodiment, the struts 112 may be formed from the same, monolithic piece of material (e.g., tube stock). Thus, reference to struts 112 may refer to different portions of the same, coextensive component. Alternatively, reference to struts 112 may refer to components that are formed separately and attached together (optionally permanently, such as by welding or soldering or other methods). In some embodiments, the struts 112 may be separate components that are detachably coupled to form proximal apices 114 and distal apices 116. Alternatively, if formed from a monolithic piece of material, the material may be cut or otherwise formed to define proximal apices 114 and distal apices 116. In some embodiments, the bend 140 in the frame 110 is formed adjacent the proximal apex 114. As illustrated in FIG. 3, if the proximal apex 114 has a configuration distinguishable from the struts 112 extending therefrom (e.g., the portions of the struts 112 forming the proximal apex 114 are closer together to form the proximal apex 114 and flare away from each other at a greater angle distal to the proximal apices 114), the bend 140 may be formed adjacent the transition between the distal end of the proximal apex 114 and the remaining more distal sections of the struts 112. In accordance with some aspects of the present disclosure, the bend 140 defining the bend-back section 142 should be positioned along the frame 110 distal to the slider 130 in at least a proximal position of the slider 120, yet positioned to be able to be captured by the sliders 120 at least when fully advanced distally. As such, distal advancement of the slider 120 over the bend-back section 142 captures the bend-back section 142 to straighten out the frame 110 to retain the same final mechanics as in a similar frame without a bend-back section 142. Therefore, in at least some embodiments, the length of the bend-back section 142 preferably is less than or equal to the length of the portion of the frame 110 that a slider 120 can advance over.

A slider 120 may be provided on one or more proximal apices 114 to adjust the configuration of the frame 110. The slider 120 may be advanced distally towards the distal end 113 of the frame 110 to bring together the struts 112 forming such proximal apex 114 to collapse the frame 110 (reduce the overall width of the frame 110) towards the collapsed configuration. The slider 120 may be retracted proximally towards the proximal end 111 of the frame 110 to allow the struts 112 to move apart to allow the frame 110 to expand as described above. As may be seen with reference to FIG. 3, in one embodiment, as illustrated, the slider screw 122 may be positioned in a window 115 in a proximal apex 114 of the frame 110. The screw 122 may be held in place with one or more bearing tabs 118 extending inwardly from the proximal apex 114 to the screw 122 (e.g., to engage a neck region in the screw) to permit rotation of the screw 122 about its rotational axis but to hold the screw 122 against axial movement, thereby advancing or retracting the slider 120 relative to the frame 110 upon rotation of the screw 122 relative to the frame 110.

To facilitate anchoring of the implantable device 100 at the treatment site TS, one or more anchor 130 are provided, such as along the distal end 113 of the frame 110 of the implantable device 100. The anchor 130 may have a latch coupler 132 similar to the slider latch coupler 122 and configured to be engaged by the latch of an actuator 1012D (illustrated in FIG. 2). In the illustrated embodiment, the anchor 130 is a helical anchor advanced or retracted by rotating the anchor 130 (e.g., by rotation of the actuator 1012D coupled thereto). However, other configurations of anchors are within the scope and spirit of the present disclosure. In some embodiments, at least one of the anchors 130 may be a collar-based anchor advanceable through an anchor housing 134 such as in the form of a collar or sleeve or the like (as known or heretofore known in the art). The anchors 130 are advanced from a retracted delivery configuration (such as illustrated in FIG. 2 with respect to the prior art implantable device 100*p*) towards the distal end 113 of the frame 110 to advance into tissue at the treatment site TS to anchor the frame 110 thereto.

Further details of examples of frames, sliders, anchors, and further components and features thereof, and associated delivery devices and methods of use may be appreciated with reference to the following patents and patent applications, each of which is incorporated herein by reference in its entirety for all purposes: U.S. Pat. No. 9,180,005, issued Nov. 10, 2015, and titled "ADJUSTABLE ENDOLUMINAL MITRAL VALVE RING"; U.S. Pat. No. 10,335,275, issued Jul. 2, 2019, and titled "METHODS FOR DELIVERY OF HEART VALVE DEVICES USING INTRAVASCULAR ULTRASOUND IMAGING"; U.S. Pat. No. 9,848, 983, issued Dec. 26, 2017, and titled "VALVE REPLACEMENT USING ROTATIONAL ANCHORS"; U.S. Pat. No. 10,555,813, issued Feb. 11, 2020, and titled "IMPLANTABLE DEVICE AND DELIVERY SYSTEM FOR RESHAPING A HEART VALVE ANNULUS"; U.S. Pat. No. 10,548,731, issued Feb. 4, 2020, and titled "IMPLANTABLE DEVICE AND DELIVERY SYSTEM FOR RESHAPING A HEART VALVE ANNULUS"; U.S. Pat. No. 9,192,471, issued Nov. 24, 2015, and titled "DEVICE FOR TRANSLUMENAL RESHAPING OF A MITRAL VALVE ANNULUS"; U.S. Patent Application Publication No. 2010/0249920, published Sep. 30, 2010, and titled "DEVICE FOR TRANSLUMENAL RESHAPING OF A MITRAL VALVE ANNULUS"; U.S. Pat. No. 9,795,480, issued Oct. 24, 2017, and titled "RECONFIGURING TISSUE FEATURES OF A HEART ANNULUS"; U.S. Pat. No. 9,610,156, issued Apr. 4, 2017, and titled "MITRAL VALVE INVERSION PROSTHESES"; and/or U.S. Pat. No. 10,321,999, issued Jun. 18, 2019, and titled "SYSTEMS AND METHODS FOR RESHAPING A HEART VALVE". Thus, the description of particular features and functionalities herein is not meant to exclude other features and functionalities, such as those described in the references incorporated herein by reference or others within the scope of the development.

Figure 5:
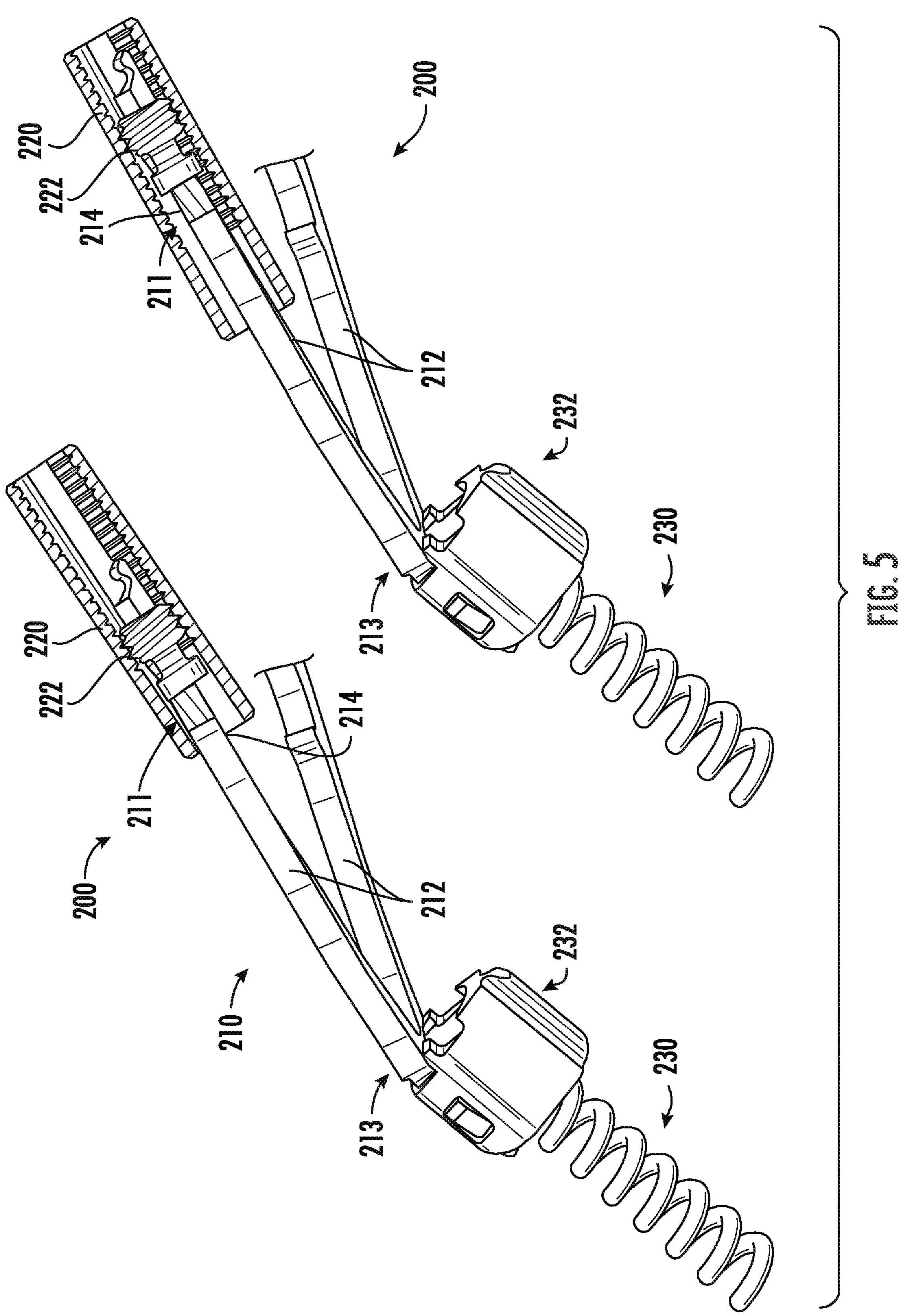
FIG. 5 is a detail view of an example of an annuloplasty device partially in cross-section to illustrate an example of a slider and a slider screw formed in accordance with principles of the present disclosure.

In accordance with another aspect of the present disclosure, as illustrated in FIG. 5, instead of (as illustrated) or in addition to having a bend 140, a portion of the implantable device 200 may move relative to another portion of the implantable device 200 to allow greater expansion of the distal end 213 of the frame 210 than achievable without such movement. In some embodiments, the relative dimensions of the slider 220 and the frame 210 may be modified to allow the desired expansion of an implantable device 200. More particularly, the clearance between the interior of the slider 220 and the frame 210 may be increased (in comparison with prior art sliders and slider screws) to allow pivoting of the slider 220 with respect to the frame 210, as may be appreciated with reference to the cross-sectional views through the slider 220 in FIG. 5. Such clearance may be increased by increasing the interior space within the slider 220 and/or reducing the thickness of the portion of the frame 210 over which the slider 220 is positioned.

In embodiments utilizing a slider screw 222 to actuate the slider 220 (such as to advance or retract to adjust the configuration of the frame 210), as illustrated, the screw 222 may pivot with respect to the frame 210 to allow pivoting of the slider 220. The screw 222 may be mounted similar to the screw 122 illustrated in FIG. 1 and FIG. 3, in a window in a proximal apex 214 of the frame 210 to pivot about bearings similar to those shown in FIG. 1 and FIG. 3. Reference is made to the above description of such mounting for the sake of brevity and convenience, with common elements with common features being indicated in FIG. 5 with similar reference numbers increased by 100. The slider 220 may be configured such that the slider screw 222 may cause the slider 220 to pivot as little as about 5° and as much as about 45° (including increments of 0.5° therebetween) with respect to the frame 210. Pivoting of the slider 220 by as little as 5° may translate into an increase in approximately 2 mm in the landing diameter of the distal end 213 of the frame 210 when coupled to a delivery device 1010 as compared with a frame with the same dimensions but without a pivoting slider. The slider 220 may pivot back to a positioned substantially aligned with the frame 210 when the frame 210 is no longer coupled to a delivery device.

In accordance with various principles of the present disclosure, pivoting of the slider 220 will allow the distal end 213 of the frame 210 to expand outwardly relative to the proximal end 211 of the frame 210 without the slider 220 disturbing the nature or shape of the frame 210 as in the prior art frame 110*p*. Such configuration of a slider 220 thus reduces the moment exerted on the frame 210 upon expansion of the frame 210 while still coupled to a delivery device 1010D. Similar improvements to the expansion dimensions of the distal end 213 of the implantable device 200 of FIG. 5 may be achieved as with the implantable device 100 of FIGS. 1, 3, and 4. As may readily be appreciated, such pivotability of the slider 220 has minimal to no impact on the fully collapsed configuration or typical cinched configurations. As the slider 220 advances distally over the frame 210, the angle of the slider 220 relative to the frame 210 decreases. Once the slider 220 is fully distally advanced over the frame 210, the slider 220 generally is straightened and barely pivots with respect to the frame 210.

As may be appreciated, implantable devices 100, 200 formed in accordance with various principles of the present disclosure generally will achieve improved opening mechanics over prior art implantable devices while replicating the mechanics of an implanted cinched configuration as in prior art implantable devices. Implantable devices 100, 200 formed in accordance with various principles of the present disclosure thus may be used with a wider range of treatment sites TS, such as larger valve annuli than may have been treated by prior art implantable devices which expand from a compact delivery configuration small enough for transluminal delivery.

It will be appreciated that an implantable device 100, 200 formed in accordance with principles of the present disclosure is not to be limited to the embodiments of components described above. For instance, although a frame formed of multiple struts and apices is described, other configurations of frames are within the scope and spirit of the present disclosure. Moreover, other configurations of elements or components used to adjust the expansion or contraction of the frame and/or to adjust the position(s) of the anchors are within the scope and spirit of the present disclosure. Principles of the present disclosure are applicable to devices designed to repair valvular regurgitation, such as mitral and tricuspid valves, but may be applied more broadly. Principles of the present disclosure may be applied to other medical devices where two or more struts are cinched together during implantation. Finally, the broad principles of the present disclosure are applicable to other implantable devices which are expanded from a collapsed delivery configuration, such as while still coupled to a delivery device which does not expand as much as the implantable device is to expand. For instance, the implantable device may be configured to reshape a cardiac feature other than a valve annulus, or may be implanted in a treatment site TS other than the heart.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. An implantable annuloplasty device configured to reshape a cardiac valve annulus, the implantable annuloplasty device being shiftable between a collapsed configuration and an expanded configuration, the implantable annuloplasty device comprising:

a tubular frame extending about a frame axis and having a proximal end configured to be coupled to a delivery device and a distal end configured to be secured to tissue;

wherein:

the tubular frame has a proximal section adjacent the proximal end of the frame, an anchoring section adjacent the distal end of the frame, and a middle section between the proximal section and the anchoring section;

the proximal section of the tubular frame bows outwardly from the frame axis at least when the implantable annuloplasty device is expanded prior to being implanted;

wherein the proximal section is disposed radially outward of the proximal end of the tubular frame at least when the implantable annuloplasty device is expanded prior to being implanted; and the anchoring section of the tubular frame extends at an angle relative to the middle section in a direction inwardly towards the frame axis.

2. The implantable annuloplasty device of claim 1, wherein a bend is provided adjacent and spaced from the proximal end of the tubular frame to define the proximal section relative to the middle section.

3. The implantable annuloplasty device of claim 2, wherein the tubular frame comprises a plurality of struts joined along proximal apices, and the bend is formed adjacent at least one of the proximal apices.

4. The implantable annuloplasty device of claim 3, further comprising a slider on the at least one proximal apex, the slider movable along the at least one proximal apex to shift the implantable device between a collapsed configuration and an expanded configuration.

5. The implantable annuloplasty device of claim 4, wherein the slider is slidable over the bend.

6. The implantable annuloplasty device of claim 1, the tubular frame comprises a plurality of struts joined along proximal apices.

7. The implantable annuloplasty device of claim 6, further comprising a slider on at least one of the proximal apices, the slider movable along the at least one proximal apex to shift the implantable device between a collapsed configuration and an expanded configuration.

8. The implantable annuloplasty device of claim 7, wherein distal movement of the slider causes the proximal section of the frame to straighten relative to the middle section of the frame.

9. The implantable device of claim 8, wherein distal movement of the slider over a bend in the frame separating the proximal section from the middle section causes the proximal section of the frame to straighten relative to the middle section of the frame.

10. The implantable device of claim 6, wherein:

a slider screw is held in a window in the at least one proximal apex by one or more bearings;

the slider is movable along the at least one apex upon rotation of the slider screw; and the slider screw pivots with respect to the at least one apex to pivot the slider with respect to the apex, the slider forming the proximal section of the tubular frame.

11. The implantable device of claim 10, wherein the slider forms the proximal section of the frame and is pivotable between a configuration at an angle relative to the middle section of the frame to a configuration substantially aligned with the middle section of the frame.

12. A delivery system comprising:

a delivery catheter;

a delivery device deliverable through the delivery catheter to a treatment site; and an implantable annuloplasty device configured to reshape a cardiac valve annulus having a proximal end coupled to the delivery device and a distal end configured to be secured to tissue at the treatment site, the implantable annuloplasty device deliverable through the delivery catheter to the treatment site;

wherein:

the delivery device comprises at least one elongated member;

the implantable annuloplasty device is expandable from a collapsed delivery configuration to an expanded deployment configuration while coupled to the delivery device;

a proximal section of the implantable annuloplasty device adjacent the proximal end of the implantable annuloplasty device remains at a smaller angle with respect to the at least one elongated member of the delivery device than does a middle section of the implantable annuloplasty device extending distally from the proximal section when the implantable annuloplasty device shifts from the collapsed delivery configuration to the expanded deployment configuration while coupled to the delivery device;

wherein the implantable annuloplasty device includes a tubular frame;

wherein an outward bend is provided adjacent and spaced from a proximal end of the tubular frame to form the proximal section of the implantable annuloplasty device;

wherein the outward bend defines a region of the tubular frame that is disposed radially outward of the proximal end of the tubular frame;

wherein an inward bend is provided adjacent and spaced from a distal end of the tubular frame to form an anchoring section of the implantable annuloplasty device and wherein the tubular frame comprises a plurality of struts joined along proximal apices, and the outward bend is formed adjacent at least one of the proximal apices.

13. The delivery system of claim 12, further comprising a slider on the at least one of the proximal apices, the slider movable along the at least one proximal apex to shift the implantable annuloplasty device between a collapsed configuration and an expanded configuration.

14. The delivery system of claim 13, wherein the slider is slidable over the outward bend.

15. The delivery system of claim 12, wherein:

the tubular frame comprises a plurality of struts joined along proximal apices;

a slider is provided on at least one of the proximal apices, the slider movable along the at least one proximal apex to shift the implantable device between a collapsed configuration and an expanded configuration;

a slider screw is held in a window in the at least one proximal apex by one or more bearings;

the slider is movable along the at least one apex upon rotation of the slider screw; and the slider screw pivots with respect to the at least one apex to pivot the slider with respect to the apex, the slider forming the proximal section of the tubular frame.

16. The delivery system of claim 12, wherein:

an anchoring bend is provided in the frame defining an anchoring section adjacent a distal end of the implantable device; and the anchoring section extends at a smaller angle with respect to the at least one elongated member of the delivery device than does the middle section of the implantable annuloplasty device.

17. An implantable annuloplasty device, comprising:

a tubular frame extending about a frame axis and having a proximal end configured to be coupled to a delivery device and a distal end configured to be secured to tissue;

wherein the tubular frame has a middle section, a proximal section extending between the proximal end of the tubular frame and the middle section, and an anchoring section extending between the middle section and the distal end of the tubular frame;

wherein the proximal section of the tubular frame bows outwardly relative to the proximal end of the tubular frame and the middle section; and wherein the anchoring section of the tubular frame extends radially inward relative to the middle section.

18. The implantable annuloplasty device of claim 17, wherein the proximal section includes a plurality of struts extending between the proximal end of the tubular frame and the middle section; and wherein in a direction extending from the proximal end of the tubular frame to the middle section, the struts bow radially outward.

* * * * *